United States Patent [19]
Tobe et al.

[11] Patent Number: 5,822,059
[45] Date of Patent: Oct. 13, 1998

[54] ATOMIC ABSORPTION SPECTROPHOTOMETER AND GRAPHITE TUBE TYPE CUVETTE USED FOR THE SAME

[75] Inventors: Hayato Tobe, Mito; Kazuo Moriya, Hitachinaka; Yoshisada Ebata, Hitachinaka; Yasushi Terui, Hitachinaka, all of Japan

[73] Assignee: Hitachi Ltd., Tokyo, Japan

[21] Appl. No.: 633,234

[22] Filed: Apr. 16, 1996

[30] Foreign Application Priority Data

Apr. 21, 1995 [JP] Japan ................... 7-096718

[51] Int. Cl.$^6$ ................... G01J 3/30
[52] U.S. Cl. ................... 356/312
[58] Field of Search ................... 356/312, 244

[56] References Cited

U.S. PATENT DOCUMENTS

4,202,628  5/1980  Koizumi et al. ................... 356/244 X

*Primary Examiner*—K. Hantis
*Attorney, Agent, or Firm*—Kenyon & Kenyon

[57] ABSTRACT

The invention intends to provide an atomic absorption spectrophotometer which can establish a uniform heat distribution during heating of a sample and can improve analysis accuracy and analyzing efficiency. For this purpose, a graphite tube type cuvette mounted in a graphite atomizer furnace for an atomic absorption spectrophotometer comprises a large-diameter portion for retaining a sample in place, a small-diameter portion connected to the large-diameter portion and having a smaller diameter than the large-diameter portion, and a step portion for demarcating between the large-diameter portion and the small-diameter portion. The graphite tube type cuvette is formed such that its cross-sectional area in a plane perpendicular to the direction of passage of an electric current supplied to the cuvette is the same in any of the large-diameter portion, the small-diameter portion and the step portion. The amount of resistance heat is thereby also the same in any portions.

36 Claims, 4 Drawing Sheets

TEMPERATURE PROGRAM

| HEATING STAGE | | TIME IN PRIOR ART | TIME IN EMBODIMENT |
|---|---|---|---|
| DRYING | 80~140°C | 40 sec | 30 sec |
| ASHING | 1000°C | 30 | 20 |
| ATOMIZATION | 2700°C | 5 | 5 |
| CLEANING | 2800°C | 4 | 4 |
| TOTAL HEATING TIME | | 79 sec | 59 sec |

ATOMIC ABSORPTION SPECTROPHOTOMETER AND GRAPHITE TUBE TYPE CUVETTE USED FOR THE SAME

BACKGROUND OF THE INVENTION

The present invention relates to an atomic absorption spectrophotometer for atomizing a sample and measuring atomic absorption of the sample for elementary analysis, and more particularly to an atomic absorption spectrophotometer which can improve analysis accuracy, and a graphite tube type cuvette mounted in a graphite atomizer furnace of the atomic absorption spectrophotometer.

Generally, an atomic absorption spectrophotometer for atomizing a sample and measuring atomic absorption of the sample is often employed to carry out elementary analysis on, e.g., metallic elements contained in the sample. In such an atomic absorption spectrophotometer, a sample is pipetted and retained in a graphite tube type cuvette mounted in a graphite atomizer furnace, and an electric current is supplied to the graphite tube type cuvette in the longitudinal direction thereof to heat the sample with resistance heat for drying, ashing and atomizing it. A light beam emitted from a light source is then irradiated to atomic vapor of the atomized sample to measure absorbance of the atomic vapor.

As described in JP, A, 3-146853, for example, the graphite tube type cuvette mounted in the graphite atomizer furnace of the atomic absorption spectrophotometer comprises a chamber (large-diameter portion) for retaining a sample in place and demarcated by a step at each of both chamber ends, and a portion (small-diameter portion) having a smaller diameter than the sample retaining chamber and connected to each of both the chamber ends. In this graphite tube type cuvette, the step demarcating the sample retaining chamber is formed to have an obtuse angle not smaller than 110 degrees between its horizontal surface and its lateral surface on the sample retaining chamber side, or the step is formed to have a spherical surface, so that the sample is prevented from spreading beyond the step to thereby improve reproducibility and analysis accuracy in the measurement.

Conventional graphite tube type cuvettes as mentioned above, by way of example, are constituted by a combination of the large-diameter portion and the small-diameter portion of which outer and inner diameters are different from each other. In some cases, the step portion is formed with a cross-sectional area being different from those of the large- and small-diameter portions to such an extent that the former's cross-sectional area is twice or more the latter's. Therefore, when an electric current is supplied to pass through the graphite tube type cuvette, resistance values are different in the respective portions of the graphite tube type cuvette and, particularly, the amount of heat produced in the step portion becomes small. Thus, the respective portions of the graphite tube type cuvette produce the different amounts of heat from each other and exhibit an uneven heat distribution.

As a result, part of the pipetted sample which is contiguous to the step portion has a lower temperature than the remaining part which is placed near the center of the large-diameter portion. This requires the sample to be heated additionally for drying, ashing and atomizing it, and hence an additional heating time. For a sample having a high melting point, the sample is more apt to remain not completely atomized in an area where the atomizing temperature is relatively low, and there often occurs a memory phenomenon which brings about an adverse effect on the measurement of a next sample. In other words, analysis accuracy is reduced. Further, because of an uneven heat distribution along the graphite tube type cuvette, all of the sample is not atomized simultaneously, which causes a loss of absorbance in the atomic absorption and deteriorates the atomization efficiency.

SUMMARY OF THE INVENTION

An object of the present invention is to solve the above-stated problem in the prior art.

To achieve the above object, the present invention is constituted to make a temperature difference between a large-diameter portion (sample retaining portion) and a step portion so small that a significant effect on the atomic absorption analysis is avoided.

More preferably, in an atomic absorption spectrophotometer comprising a graphite tube type cuvette which comprises a large-diameter portion for retaining a sample in place, a small-diameter portion connected to the large-diameter portion and having a smaller diameter than the large-diameter portion, and a step portion for demarcating between the large-diameter portion and the small-diameter portion, and a graphite atomizer furnace for supplying an electric current to the graphite tube type cuvette and atomizing the sample with resistance heat, thereby analyzing atomic absorption of the sample, the graphite tube type cuvette is formed such that its cross-sectional area in a plane perpendicular to the direction of passage of the electric current supplied from the graphite atomizer furnace is the same in any of the large-diameter portion, the small-diameter portion and the step portion.

With such an arrangement, the large-diameter portion for retaining a sample in place, the small-diameter portion connected to the large-diameter portion and having a smaller diameter than the large-diameter portion, and the step portion for demarcating between the large-diameter portion and the small-diameter portion have equal cross-sectional areas in any portions in a plane perpendicular to the direction of passage of the supplied electric current. This provides the same resistance value in the direction of passage of the supplied electric current in any of the large-diameter portion, the small-diameter portion and the step portion. Therefore, when the graphite tube type cuvette is heated with resistance heat by supplying an electric current therethrough, the amount of resistance heat is the same in any portions of the cuvette and a heat distribution becomes uniform along the entire cuvette.

Accordingly, since the sample retained in the graphite tube type cuvette is uniformly heated without being partly less heated to a lower temperature, there is neither the need of heating the sample additionally for drying, ashing and atomizing it, nor the need of prolonging the heating time additionally. Even for a sample having a high melting point, no sample remains not completely atomized and a memory phenomenon ascribed is prevented. Further, since a heat distribution is uniform along the graphite tube type cuvette during the atomization, all of the sample is atomized simultaneously and no loss of absorbance will occur in the atomic absorption.

DETAILED DESCRIPTION OF THE PREFERRED EMBODIMENT

A preferred embodiment of the present invention will be described hereinafter.

First, the entire configuration of an atomic absorption spectrophotometer will be described by referring to FIG. 1.

Figure 1:
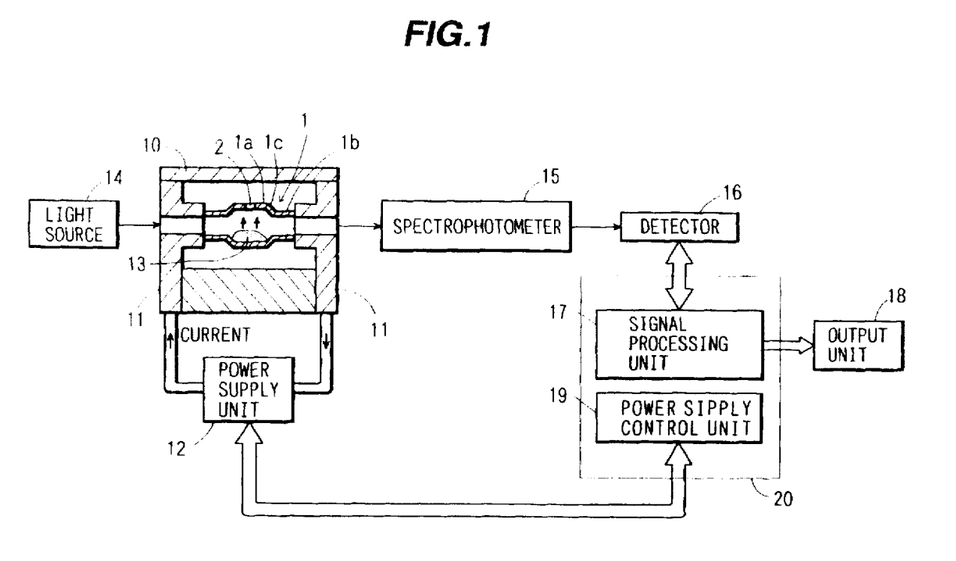
FIG. 1 is a schematic view showing the entire configuration of an atomic absorption spectrophotometer according to one embodiment of the present invention.

FIG. 1 is a schematic view showing the entire configuration of an atomic absorption spectrophotometer according to one embodiment of the present invention. In the illustrated atomic absorption spectrophotometer, a graphite tube type cuvette 1 is attached between a pair of electrodes 11 of a graphite atomizer furnace 10, and the electrodes 11 are connected to a power supply unit 12. A sample 13 to be measured is pipetted and retained in a large-diameter portion 1a of the graphite tube type cuvette 1 through a window 2. When an electric current is supplied to the electrodes 11 from the power supply unit 12, the graphite tube type cuvette 1 produces resistance heat to heat the sample 13. Then, the sample 13 is converted into atomic vapor through successive heating stages for drying, ashing and atomizing it.

A light beam emitted from a light source 14 is irradiated to the atomic vapor in the graphite tube type cuvette 1, and the light having passed through the graphite tube type cuvette 1 is absorbed partly in wavelength specific to the sample 13 by atomic absorption. The light having been subject to the atomic absorption enters a spectrophotometer 15 for dispersion, and only part of the light to be measured is introduced to a detector 16. Detection data from the detector 16 is transmitted to a signal processing unit 17 where the absorbance of the sample 13 is measured through arithmetic and other processing steps. A measured result is output to an output unit 18. When the measurement of one sample 13 is completed, the heating is further continued to remove the residue of the sample 13.

In the above measurement process, values of current and voltage supplied from the power supply unit 12, etc. are controlled by a power supply control unit 19. Further, the signal processing unit 17 and the power supply control unit 19 are integrated together into a central processing unit 20.

Figure 2:
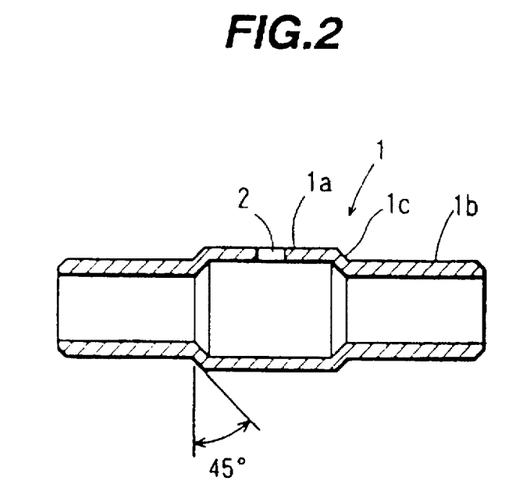
FIG. 2 is a sectional view showing a graphite tube type cuvette of a graphite atomizer furnace for the atomic absorption spectrophotometer shown in FIG. 1.

FIG. 2 is a sectional view showing the graphite tube type cuvette of this embodiment. As shown in FIG. 2, the graphite tube type cuvette 1 comprises a large-diameter portion 1a for retaining a sample in place, a small-diameter portion 1b connected to each of both ends of the large-diameter portion 1a and having a smaller diameter than the large-diameter portion 1a, and a step portion 1c for demarcating between the large-diameter portion 1a and the small-diameter portion 1b. The respective portions of the graphite tube type cuvette 1 are all made of the same graphite. In this embodiment, the step portion 1c is inclined at an angle of 45°.

The electric current for heating is supplied to pass through the graphite tube type cuvette 1 in the longitudinal or axial direction thereof. The graphite tube type cuvette 1 is formed such that the large-diameter portion 1a, the small-diameter portion 1b and the step portion 1c have equal cross-sectional areas in the longitudinal or axial direction of the cuvette in any portions, i.e., in any planes perpendicular to the direction of passage of the supplied electric current. In other words, when the graphite tube type cuvette 1 is cut crosswise in any plane perpendicular to the longitudinal direction of the cuvette, the cuvette has the same cross-sectional area. Accordingly, the large-diameter portion 1a, the small-diameter portion 1b and the step portion 1c of the graphite tube type cuvette 1 have equal resistance values in the direction of passage of the supplied electric current in any portions. As a result, when the graphite tube type cuvette 1 is heated upon the supply of the electric current, the respective portions of the graphite tube type cuvette 1 produce the same amount of heat and hence a heat distribution becomes uniform along the entire cuvette.

The large-diameter portion 1a has formed therein a small window 2 through which a sample is pipetted and retained in the large-diameter portion 1a. The presence of the window 2 reduces the cross-sectional area of the large-diameter portion 1a in its part, but a resulting reduction in the cross-sectional area is very small and within an allowable error range. To ensure higher accuracy in uniformity of the cross-sectional area, the large-diameter portion 1a may be, for example, thickened partly to such an extent as just compensating for the area of the window 2.

Figure 3:
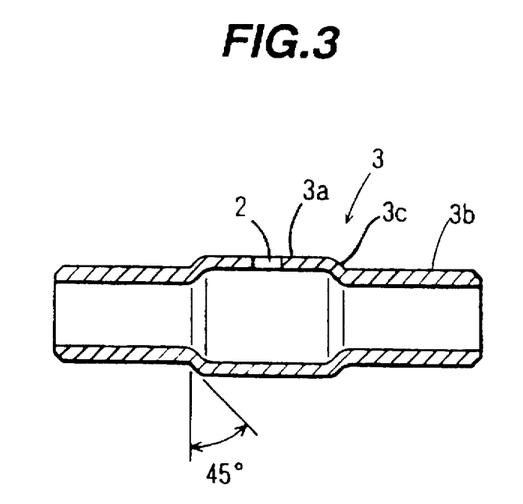
FIG. 3 is a sectional view of another graphite tube type cuvette modified such that the boundary between a step portion and a large-diameter portion and the boundary between the step portion and a small-diameter portion are each defined by a curved surface.

FIG. 3 is a sectional view of another graphite tube type cuvette 3 modified differently from the cuvette of FIG. 2 in that the boundary between a step portion 3c and a large-diameter portion 1a and the boundary between the step portion 3c and a small-diameter portion 3b are each defined by a curved surface. The remaining configuration is the same as the graphite tube type cuvette 1 of FIG. 2. Of course, the large-diameter portion 3a, the small-diameter portion 3b and the step portion 3c are formed to have equal cross-sectional areas in the longitudinal direction of the cuvette in any portions, i.e., in any planes perpendicular to the direction of passage of the supplied electric current, and therefore have equal resistance values in the direction of passage of the supplied electric current in any portions. While any one of the graphite tube type cuvettes shown in FIGS. 2 and 3 may be used in this embodiment, the following description will be made as using the graphite tube type cuvette shown in FIG. 2.

In the measurement performed by utilizing an atomic absorption spectrophotometer, it is important that a heat distribution along the graphite tube type cuvette 1 be uniform. If not uniform, elementary analysis could not be achieved with high accuracy and high efficiency. In this embodiment, since the large-diameter portion 1a, the small-diameter portion 1b and the step portion 1c of the graphite tube type cuvette 1 have equal resistance values in any portions, the same amount of heat is produced in the respective portions of the graphite tube type cuvette 1 and a heat distribution becomes uniform along the entire cuvette. Therefore, the sample 13 is uniformly heated without being partly less heated to a lower temperature. This eliminates the need of heating the sample additionally for drying, ashing and atomizing it, and also the need of prolonging the heating time additionally. Even for the sample 13 having a high melting point, the sample is uniformly heated and hence uniformly atomized so that no sample will remain not completely atomized. As a result, a memory phenomenon otherwise caused by the residue of a previous sample affecting the measurement of a next sample is essentially prevented. Furthermore, since a heat distribution is uniform along the graphite tube type cuvette 1 during the atomization, all of the sample 13 is atomized simultaneously and no loss of absorbance will occur in the atomic absorption.

Figure 4:
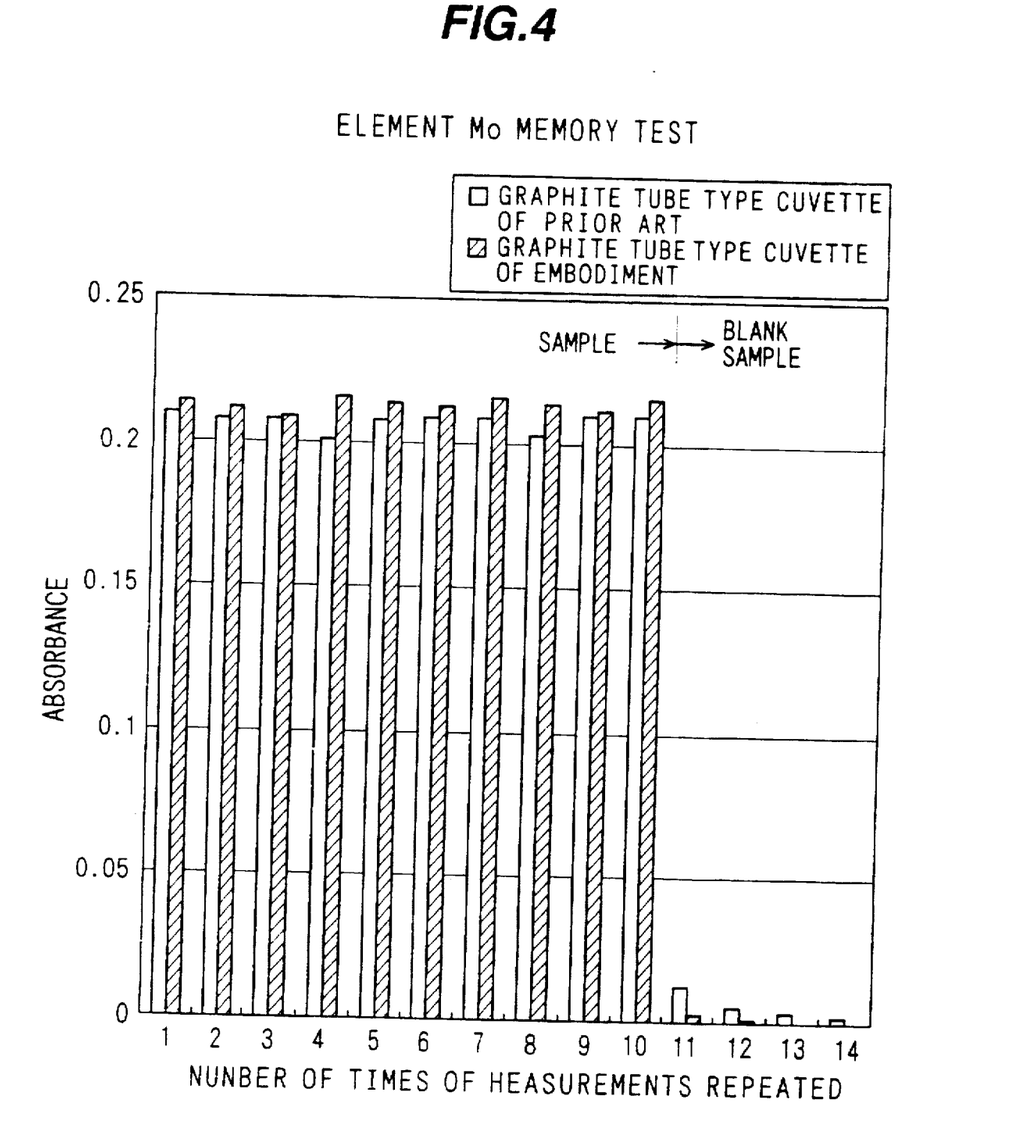
FIG. 4 is a graph showing results of an element Mo memory test made by utilizing the atomic absorption spectrophotometer shown in FIG. 1.
Figure 5:
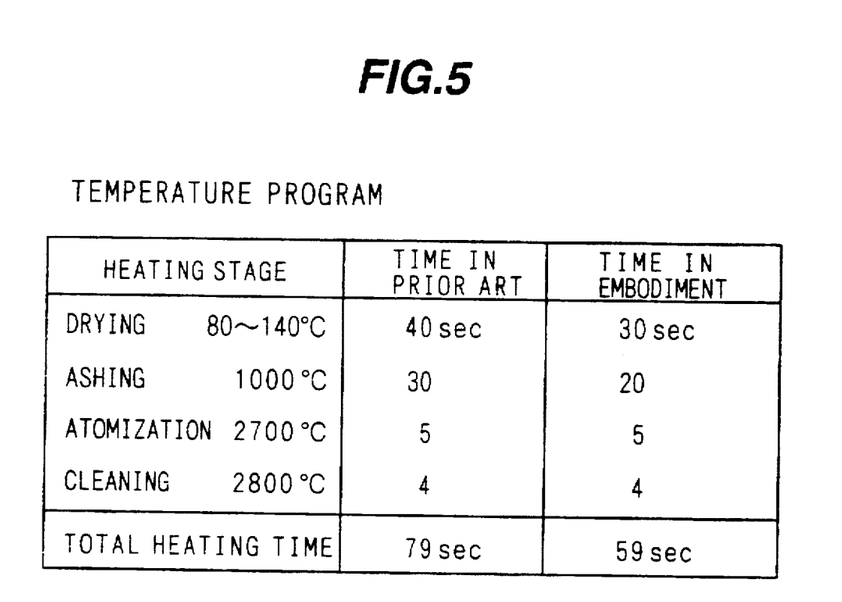
FIG. 5 is a table showing a temperature program for heating a sample and heating times required in respective stages.

FIG. 4 is a graph showing results of an element Mo memory test made by utilizing the atomic absorption spectrophotometer of this embodiment, and FIG. 5 is a table showing a temperature program for heating a sample in the test of FIG. 4 and heating times required in respective stages. The test results were obtained by repeating the measurement ten times successively while replacing a 40 ppb sample of 20 microliter for each of the measurements, and then measuring a blank sample three times.

Since the 11th and subsequent measurements in FIG. 4 are conducted for the blank sample, the test results that the absorbance is measured for the blank sample in those measurements mean that there occurs a memory phenomenon, and the fact that the absorbance measured in the 11th and subsequent measurements is as small as possible means that the elementary analysis can be achieved with higher accuracy. By using the graphite tube type cuvette of this embodiment, the absorbance measured for the blank sample in the 11th measurement could be reduced down to 20% of that measured by using the graphite tube type cuvette of the prior art. In other words, this embodiment succeeded in reducing the effect of a memory phenomenon down to 20% of that occurred in the prior art. Further, as will be seen from the table of FIG. 5, by using the graphite tube type cuvette of this embodiment, the heating times required in the respective stages for heating the sample could be shortened and the total heating time could be cut down about 20 seconds as compared with that required in the prior art.

In the foregoing embodiment, the respective portions of the graphite tube type cuvette are all made of the same graphite so that the same specific resistance is provided in any portions. But, for example, when the large-diameter portion, the small-diameter portion and the step portion are made of materials having different specific resistances from each other, the present invention may also be practiced by forming the graphite tube type cuvette so as to have equal resistance values in any portions per unit thickness in the longitudinal direction of the cuvette, i.e., to produce the same amount of resistance heat in any plane perpendicular to the direction of passage of the supplied electric current of the prior art.

As described above, since the cross-sectional area of the graphite tube type cuvette 1 in a plane perpendicular to the direction of passage of the supplied electric current is the same in any portions of the cuvette, the amount of resistance heat is also the same in any portions and a heat distribution can be made uniform along the entire cuvette. Accordingly, there is neither the need of heating the sample 13 additionally for atomizing it, nor the need of prolonging the heating time additionally. Even for the sample 13 having a high melting point, a memory phenomenon otherwise caused by the residue of the sample 13 being remained not completely atomized can be prevented, resulting in improved analysis accuracy. Further, since all of the sample 13 is atomized simultaneously, no loss of absorbance will occur in the atomic absorption and the analyzing efficiency can be improved.

In short, since the graphite tube type cuvette is formed to have the same cross-sectional area in a plane perpendicular to the direction of passage of the supplied electric current in any of the large-diameter portion, the small-diameter portion and the step portion thereof, any portions of the cuvette can produce the same amount of resistance heat to provide a uniform heat distribution along the entire cuvette. This eliminates the need of heating the sample additionally, and also the need of prolonging the heating time additionally. There will not occur a memory phenomenon ascribed to the residue of the sample being remained not completely atomized, resulting in improved analysis accuracy. Further, no loss of absorbance will occur in the atomic absorption and the analyzing efficiency can be improved.

What is claimed is:

1. An atomic absorption spectrophotometer comprising a graphite tube cuvette which comprises a large-diameter portion for retaining a sample in place, a small-diameter portion connected to said large-diameter portion, and a step portion for demarcating between said large-diameter portion and said small-diameter portion, and a graphite atomizer furnace for supplying an electric current to said graphite tube cuvette and atomizing said sample with resistance heat, thereby analyzing atomic absorption of said sample, wherein:

a resistance value of a portion through which the electric current is supplied from said graphite atomizer furnace is substantially the same in any of said large-diameter portion, said small-diameter portion and said step portion.

2. A graphite tube cuvette comprising a large-diameter portion for retaining a sample in place, a small-diameter portion connected to said large-diameter portion and having a smaller diameter than said large-diameter portion, and a step portion for demarcating between said large-diameter portion and said small-diameter portion, said graphite tube cuvette being mounted in a graphite atomizer furnace for an atomic absorption spectrophotometer for analyzing atomic absorption of said sample, wherein:

a resistance value of a portion through which a supplied electric current passes is substantially the same in any of said large-diameter portion, said small-diameter portion and said step portion.

3. An atomic absorption spectrophotometer including a retaining portion for retaining a sample, said sample being heated to be atomized for atomic absorption analysis of said sample, wherein said spectrophotometer further includes a small-diameter portion having a smaller diameter than said sample retaining portion and a step portion connecting said small-diameter portion and said sample retaining portion, and said step portion includes a contact portion contacting said sample, and said contacting portion and said retaining portion have substantially equal cross-section area in a plane perpendicular to a direction of electric current flowing through said step portion and said retaining portion.

4. An atomic absorption spectrophotometer according to claim 3, wherein a difference between the temperature of said step portion and the temperature of said sample retaining portion is made so small as not to affect the atomic absorption analysis due to thermal instability caused by the atomization of said sample.

5. An atomic absorption spectrophotometer according to claim 3, wherein an inner peripheral surface of said step portion is inclined.

6. An atomic absorption spectrophotometer according to claim 5, wherein an outer peripheral surface of said step portion is inclined.

7. An atomic absorption spectrophotometer according to claim 3, wherein the temperature of said step portion and the temperature of said sample retaining portion are made substantially equal to each other.

8. An atomic absorption spectrophotometer according to claim 5, wherein an inner peripheral surface of said step portion and an inner peripheral surface of said sample retaining portion are connected to each other through a surface having a curvature.

9. An atomic absorption spectrophotometer including a retaining portion for retaining a sample, said sample being heated to be atomized for atomic absorption analysis of said sample, wherein said spectrophotometer further includes a small-diameter portion having a smaller diameter than said sample retaining portion and a step portion connecting said small-diameter portion and said sample retaining portion, and said step portion includes a contact portion contacting said sample, and said contacting portion and said retaining portion have substantially equal resistance value in a direction of electric current flowing through said step portion and said retaining portion.

10. An atomic absorption spectrophotometer according to claim 9, wherein an inner peripheral surface of said step portion is inclined.

11. An atomic absorption spectrophotometer according to claim 10, wherein an outer peripheral surface of said step portion is inclined.

12. An atomic absorption spectrophotometer according to claim 9, wherein the temperature of said step portion and the temperature of said sample retaining portion are made substantially equal to each other.

13. An atomic absorption spectrophotometer according to claim 10, wherein an inner peripheral surface of said step portion and an inner peripheral surface of said sample retaining portion are connected to each other through a surface having a curvature.

14. An atomic absorption spectrophotometer according to claim 9, wherein a difference between the temperature of said step portion and the temperature of said sample retaining portion is made so small as not to affect the atomic absorption analysis due to thermal instability caused by the atomization of said sample.

15. An atomic absorption spectrophotometer including a retaining portion for retaining a sample, said sample being heated to be atomized for atomic absorption analysis of said sample, wherein said spectrophotometer further includes a small-diameter portion having a smaller diameter than said sample retaining portion and a step portion connecting said small-diameter portion and said sample retaining portion, and said step portion includes a contact portion contacting said sample, and said contacting portion and said small-diameter portion have substantially equal cross-section area in a plane perpendicular to a direction of electric current flowing through said step portion and said retaining portion.

16. An atomic absorption spectrophotometer according to claim 15, wherein a difference between the temperature of said step portion and the temperature of said small-diameter portion is made so small as not to affect the atomic absorption analysis due to thermal instability caused by the atomization of said sample.

17. An atomic absorption spectrophotometer according to claim 15, wherein an inner peripheral surface of said step portion is inclined.

18. An atomic absorption spectrophotometer according to claim 17, wherein an inner peripheral surface of said step portion and an inner peripheral surface of said small-diameter portion are connected to each other through a surface having a curvature.

19. An atomic absorption spectrophotometer according to claim 17, wherein the temperature of said step portion and the temperature of said sample retaining portion are made substantially equal to each other.

20. An atomic absorption spectrophotometer according to claim 15, wherein the temperature of said step portion and the temperature of said small-diameter portion are made substantially equal to each other.

21. An atomic absorption spectrophotometer according to claim 15, wherein a difference between the temperature of said step portion and the temperature of said sample retaining portion is made so small as not to substantially affect the atomic absorption analysis.

22. An atomic absorption spectrophotometer including a retaining portion for retaining a sample, said sample being heated to be atomized for atomic absorption analysis of said sample, wherein said spectrophotometer further includes a small-diameter portion having a smaller diameter than said sample retaining portion and a step portion connecting said small-diameter portion and said sample retaining portion, and said step portion includes a contact portion contacting said sample, and said contacting portion and said small-diameter portion have substantially equal resistance value in a direction of electric current flowing through said step portion and said retaining portion.

23. An atomic absorption spectrophotometer according to claim 22, wherein an inner peripheral surface of said step portion is inclined.

24. An atomic absorption spectrophotometer according to claim 22, wherein the temperature of said step portion and the temperature of said small-diameter portion are made substantially equal to each other.

25. An atomic absorption spectrophotometer according to claim 23, wherein an inner peripheral surface of said step portion and an inner peripheral surface of said small-diameter portion are connected to each other through a surface having a curvature.

26. An atomic absorption spectrophotometer according to claim 22, wherein a difference between the temperature of said step portion and the temperature of said sample retaining portion is made so small as not to substantially affect the atomic absorption analysis.

27. An atomic absorption spectrophotometer according to claim 23, wherein the temperature of said step portion and the temperature of said sample retaining portion are made substantially equal to each other.

28. An atomic absorption spectrometer according to claim 22, wherein a difference between the temperature of said step portion and the temperature of said small-diameter portion is made so small as not to affect the atomic absorption analysis due to thermal instability caused by the atomization of said sample.

29. An atomic absorption spectrophotometer including a graphite tube cuvette having a retaining portion for retaining a sample, said sample being heated to be atomized for atomic absorption analysis of said sample, wherein said graphite tube cuvette includes a small-diameter portion having a smaller diameter than said sample retaining portion and a step portion connecting said small-diameter portion and said sample retaining portion, and said step portion includes a contact portion contacting said sample, and said contacting portion and said retaining portion have substantially equal cross-section area in a plane perpendicular to a direction of electric current flowing through said step portion and said retaining portion.

30. An atomic absorption spectrophotometer according to claim 29, wherein a difference between the temperature of said step portion and the temperature of said sample retaining portion is made so small as not to affect the atomic absorption analysis due to thermal instability caused by the atomization of said sample.

31. An atomic absorption spectrophotometer including a graphite tube cuvette having a retaining portion for retaining a sample, said sample being heated to be atomized for atomic absorption analysis of said sample, wherein said graphite tube cuvette includes a small-diameter portion having a smaller diameter than said sample retaining portion and a step portion connecting said small-diameter portion and said sample retaining portion, and said step portion includes a contact portion contacting said sample, and said contacting portion and said retaining portion have substantially equal resistance value in a direction of electric current flowing through said step portion and said retaining portion.

32. An atomic absorption spectrometer according to claim 31, wherein a difference between the temperature of said step portion and the temperature of said sample retaining portion is made so small as not to affect the atomic absorption analysis due to thermal instability caused by the atomization of said sample.

33. An atomic absorption spectrophotometer including a graphite tube cuvette having a retaining portion for retaining a sample, said sample being heated to be atomized for atomic absorption analysis of said sample, wherein said graphite tube cuvette includes a small-diameter portion having a smaller diameter than said sample retaining portion and a step portion connecting said small-diameter portion and said sample retaining portion, and said step portion includes a contact portion contacting said sample, and said contacting portion and said small-diameter portion have substantially equal cross-section area in a plane perpendicular to a direction of electric current flowing through said step portion and said small-diameter portion.

34. An atomic absorption spectrophotometer according to claim 33, wherein a difference between the temperature of said step portion and the temperature of said small-diameter portion is made so small as not to affect the atomic absorption analysis due to thermal instability caused by the atomization of said sample.

35. An atomic absorption spectrophotometer including a graphite tube cuvette having a retaining portion for retaining a sample, said sample being heated to be atomized for atomic absorption analysis of said sample, wherein said graphite tube cuvette includes a small-diameter portion having a smaller diameter than said sample retaining portion and a step portion connecting said small-diameter portion and said sample retaining portion, and said step portion includes a contact portion contacting said sample, and said contacting portion and said small-diameter portion have substantially equal resistance value in a direction of electric current flowing through said step portion and said retaining portion.

36. An atomic absorption spectrophotometer according to claim 35, wherein a difference between the temperature of said step portion and the temperature of said small-diameter portion is made so small as not to affect the atomic absorption analysis due to thermal instability caused by the atomization of said sample.

* * * * *

UNITED STATES PATENT AND TRADEMARK OFFICE
CERTIFICATE OF CORRECTION

PATENT NO. : 5,822,059                    Page 1 of 2
DATED      : October 13, 1998
INVENTOR(S): Hayato Tobe, et. al.

It is certified that error appears in the above-identified patent and that said Letters Patent is hereby corrected as shown below:

In the Title Page: in the drawing Fig.: Change POWER SIPPLY" to --POWER SUPPLY--.

In the Drawings: Sheet 1 of 4, change (19) "POWER SIPPLY" to --POWER SUPPLY--.

Sheet 3 of 4, last line: Change "NUNBER" to --NUMBER--; change "HEASUREMENTS" to --MEASUREMENTS--.

| Column | Line | |
|---|---|---|
| 1 | 25 | Before "atomic" insert --the--. |
| 3 | 2 | Change "between a step" to --between the step--. |
| 3 | 38 | Change "in wavelength" to --in a wavelength--. |
| 3 | 39 | After "absorption." delete ",". |
| 4 | 44 | After "made" delete "as". |
| 5 | 25 | Delete "down". |

UNITED STATES PATENT AND TRADEMARK OFFICE
CERTIFICATE OF CORRECTION

PATENT NO. : 5,822,059
DATED : October 13, 1998
INVENTOR(S) : Hayato Tobe, et. al.

It is certified that error appears in the above-identified patent and that said Letters Patent is hereby corrected as shown below:

| Column | Line | |
|--------|------|---|
| 5 | 28 | Delete "down"; change "occurred" to --observed--. |
| 5 | 56 | Change "being remained" to --remaining--. |
| 6 | 6 | Change "being remained" to --remaining--. |
| 6 | 47 | Change "area" to --areas--. |
| 7 | 13 | Change "value" to --values--. |
| 7 | 45 | Change "area" to --areas--. |
| 8 | 17 | Change "value" to --values--. |
| 8 | 57 | Change "area" to --areas--. |
| 9 | 27 | Change "area" to --areas--. |

Signed and Sealed this

Thirtieth Day of November, 1999

Attest:

Q. TODD DICKINSON

*Attesting Officer*      *Acting Commissioner of Patents and Trademarks*